US010449041B2

United States Patent
Modine

(10) Patent No.: US 10,449,041 B2
(45) Date of Patent: Oct. 22, 2019

(54) MITRAL OR TRICUSPID HEART VALVE PROSTHESIS

(71) Applicant: Valmy Holding, Villeneuve d'Ascq (FR)

(72) Inventor: Thomas Modine, La Madeleine (FR)

(73) Assignee: VALMY HOLDING, Villeneuve D'Ascq (FR)

( * ) Notice: Subject to any disclaimer, the term of this patent is extended or adjusted under 35 U.S.C. 154(b) by 0 days.

(21) Appl. No.: 15/773,037

(22) PCT Filed: Nov. 12, 2015

(86) PCT No.: PCT/IB2015/058754
§ 371 (c)(1),
(2) Date: May 2, 2018

(87) PCT Pub. No.: WO2017/081516
PCT Pub. Date: May 18, 2017

(65) Prior Publication Data
US 2018/0325662 A1 Nov. 15, 2018

(51) Int. Cl.
*A61F 2/24* (2006.01)
(52) U.S. Cl.
CPC .......... *A61F 2/2418* (2013.01); *A61F 2/2412* (2013.01); *A61F 2/2487* (2013.01);
(Continued)
(58) Field of Classification Search
CPC ............................ A61F 2/2418; A61F 2/2487
See application file for complete search history.

(56) References Cited

U.S. PATENT DOCUMENTS

2009/0125104 A1    5/2009  Hoffman
2012/0271398 A1*  10/2012  Essinger ............... A61F 2/2412
                                                    623/1.11

FOREIGN PATENT DOCUMENTS

EP    2478868 A1    7/2012
FR    3021209 A1   11/2015
(Continued)

OTHER PUBLICATIONS

The International Search Report and the Written Opinion for PCT/IB2015/058754, ISA/EPO, The Netherlands, dated Aug. 2, 2016.
(Continued)

*Primary Examiner* — Suba Ganesan
(74) *Attorney, Agent, or Firm* — M&B IP Analysts, LLC

(57) ABSTRACT

The disclosed embodiments relate to a mitral or tricuspid heart valve prosthesis that includes. An expansible tubular frame and a prosthetic valve mounted on the frame. The frame includes an atrial portion, a ventricular portion, and an annular portion located between said atrial and ventricular portions, wherein: the atrial portion is made up of three or four metal-wire extensions, regularly distributed on the circumference of said atrial portion and projecting from said annular portion, each extension being made up of a single upside-down U-shaped or V-shaped wire and the various extensions being substantially part of an imaginary truncated sphere placed above said annular portion. The annular portion is made up of diamond meshes which comprise anchoring points; and said ventricular portion is made up of three or four extensions equivalent to the extensions, substantially contained inside an imaginary ovoid shape placed under said annular portion.

8 Claims, 2 Drawing Sheets

(52) U.S. Cl.
CPC ............ *A61F 2220/0016* (2013.01); *A61F 2230/0054* (2013.01); *A61F 2230/0071* (2013.01); *A61F 2230/0076* (2013.01)

(56) References Cited

FOREIGN PATENT DOCUMENTS

| | | |
|---|---|---|
| WO | 2009045334 A1 | 4/2009 |
| WO | 2009108615 A1 | 9/2009 |
| WO | 2009132187 A1 | 10/2009 |
| WO | 2011051043 A1 | 5/2011 |
| WO | 2013037519 A1 | 3/2013 |
| WO | 2015052663 A1 | 4/2015 |

OTHER PUBLICATIONS

The Preliminary Search Report for FR 1454680 dated Jul. 21, 2014, France.

\* cited by examiner

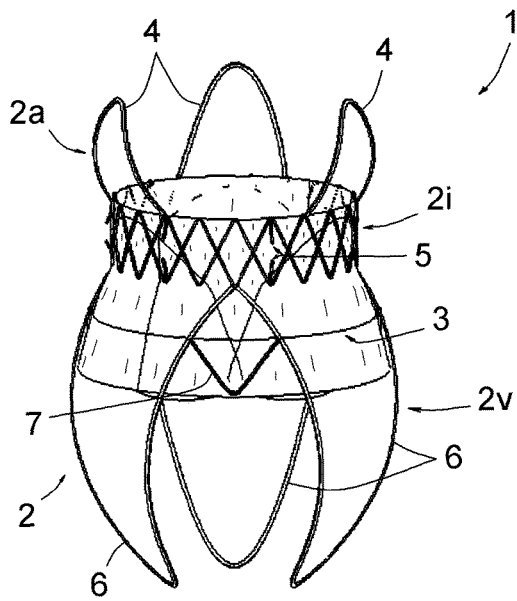
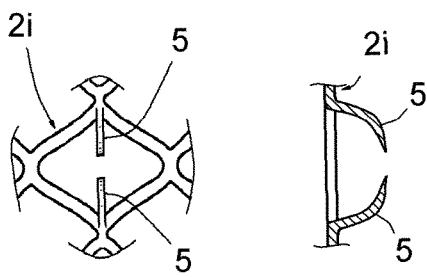
FIG. 2a    FIG. 2b
FIG. 1
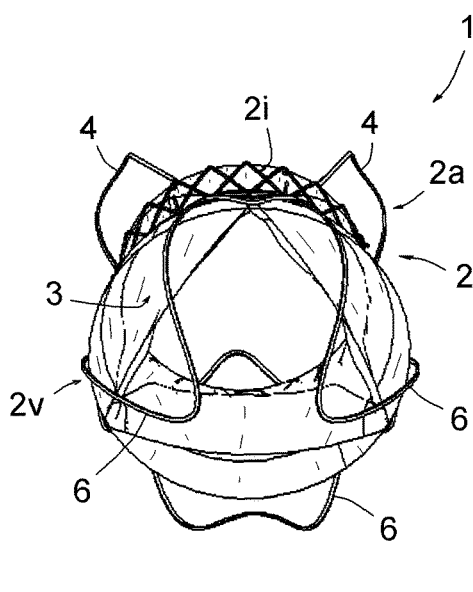
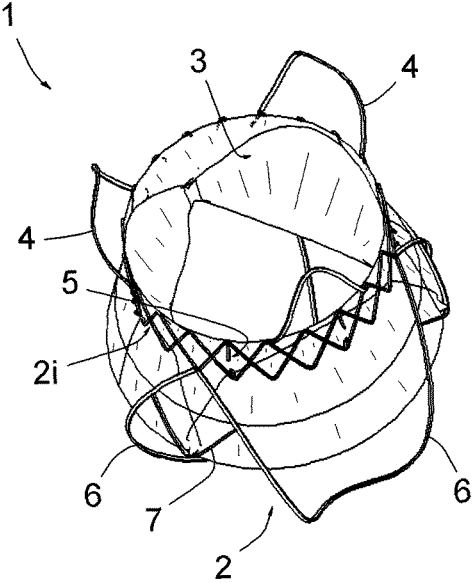
FIG. 3    FIG. 4

MITRAL OR TRICUSPID HEART VALVE PROSTHESIS

TECHNICAL FIELD

The present invention relates to a mitral or tricuspid heart valve prosthesis.

BACKGROUND

One well-known pathology of a heart valve, primarily affecting elderly patients, is the distention of the valve annulus, this distention leading to a poor coaptation of the valves and thus a loss of sealing and effectiveness of the valve.

It is known to treat this pathology by annuloplasty, i.e., by placing a total or partial prosthetic annulus aiming to recalibrate the native valve annulus. This technique has certain drawbacks, in particular not being very suitable for elderly patients.

It is also known to implant, above the native valve, a prosthesis comprising an expandable tubular frame and a prosthetic valve mounted on this frame. The tubular frame, frequently called "stent", has a mesh structure, and comprises an atrial portion, i.e., intended to be placed at the atrium of a heart, a ventricular portion, i.e., intended to be placed at the ventricle of a heart, and an annular portion, i.e., intended to be placed at the native valve annulus, situated between these atrial and ventricular portions. The frame may be self-expandable (in particular being made from a shape memory material) or made from an expandable material using a balloon. The prosthetic valve may in turn be made from a synthetic or natural material.

Such a prosthesis is deformable so as to be able to be placed in a catheter and is intended to be deployed from this catheter at the native valve to be treated. It may be placed using the apical approach (i.e., from the lower tip of the heart) or using a transseptal (mitral valve) or jugular or femoral (tricuspid valve) approach.

The existing prostheses of this type are not fully satisfactory, in particular having risks of migration and therefore obstruction of the ventricular ejection path, having a placement that is not always very easy to perform, not having a shape perfectly suited to that of the implantation site, and involving arranging an access orifice to the implantation site with a relatively large diameter, and which is therefore relatively traumatic.

The present invention primarily aims to resolve these essential drawbacks. It in particular aims to provide a prosthesis able to be inserted into a heart through an orifice having a diameter of about 18 mm, versus 22 mm with the existing prostheses.

SUMMARY

The prosthesis in question is of the aforementioned type, comprising an expandable tubular frame and a prosthetic valve mounted on the frame, said frame comprising an atrial portion, a ventricular portion and an annular portion situated between these atrial and ventricular portions.

According to the invention, said atrial portion is made up of three or four metal-wire extensions, regularly distributed on the circumference of this atrial portion and projecting from said annular portion, each extension being made up of a single upside-down U-shaped or V-shaped wire and developing with a curved shape such that in the expansion state of the prosthesis, the base of this extension is oriented radially toward the outside of said annular portion, then the extension curves toward the inside of the frame, such that the various extensions are substantially part of an imaginary truncated sphere placed above said annular portion;

said annular portion is made up of diamond meshes connected to one another by their corners, which comprise anchoring points protruding from its outer face; and said ventricular portion is made up of three or four metal-wire extensions, regularly distributed on the circumference of this ventricular portion and projecting from said annular portion, each extension being made up of a single U-shaped or V-shaped wire and developing with a curved shape such that in the expansion state of the prosthesis, the base of this extension is oriented radially toward the outside of said annular portion, then the extension curves toward the inside of the frame, such that the various extensions are substantially part of an imaginary ovoid placed below said annular portion.

The prosthesis according to the present invention thus comprises a mesh structure only at its annular portion, which, being made up of diamond meshes, is able to assume a radially contracted shape with a small diameter, smaller than 18 mm in the contracted state, when the filaments making up these meshes are in the immediate vicinity of one another; said atrial portion and said ventricular portion are not formed by a mesh structure and, by lateral contraction of the U-shaped or V-shaped wires of the extensions making them up, are also able to assume a radially contracted shape with a relatively small diameter, smaller than 18 mm in the contracted state.

The prosthesis thus formed is therefore able to be placed in a catheter having an outer diameter of about 18 mm, the insertion of which is significantly less traumatic for the cardiac wall than a catheter according to the prior art.

When the prosthesis is placed using the apical approach, its atrial portion is first deployed and brought against the atrial part of the valve annulus; the substantially spherical shape of this atrial portion is well suited to wide bearing against this atrial part of the annulus and against the adjacent wall of the atrium; said annular portion is next deployed, which leads the different anchoring points comprised by this annular portion to be inserted into the valve annulus. The continued withdrawal of the catheter causes the gradual deployment of the ventricular portion; this portion, in light of its ovoid shape, becomes closely applied against the ventricular part of the valve annulus and is well suited to the shape of the ventricle near this annulus; it does not conflict with the underlying anatomical structures. Furthermore, the independence of the aforementioned extensions making up this ventricular portion allows this ventricular portion not to present any risk of excessive bearing against the wall of the ventricle at the aortic valve, which could hinder the working of this aortic valve or obstruct the ventricular flush chamber.

The prosthesis thus structured therefore makes it possible to achieve the aforementioned aim perfectly of providing a prosthesis able to be introduced into a heart through an orifice having a diameter of about 18 mm, while having low migration risks, relatively easy placement and a shape adapted to that of the implantation site.

It should be noted that the prosthesis according to the invention could be implanted using a transseptal (mitral valve) or jugular or femoral (tricuspid valve) approach, in which case the ventricular portion is deployed first and the atrial portion is deployed second.

Preferably, said anchoring points are in the form of curved claws developing toward the outside of the said annular portion from their bases toward their pointed free ends.

The anchoring points thus configured produce effective anchoring.

The anchoring points are preferably present on the entire circumference of said annular portion; they are preferably regularly distributed on this circumference.

Preferably, the anchoring points are arranged in pairs, such that one of the anchoring points of a pair is located on the atrial side of the prosthesis and protrudes toward the ventricular side of this prosthesis, and the other anchoring point of the same pair is located on the ventricular side of the prosthesis and protrudes toward the atrial side of this prosthesis, the free ends of these anchoring points being located opposite one another, and the anchoring points of the same pair being curved, with their concave side on the inside of this pair such that the two anchoring points of the same pair of points assume the form of a "crab claw".

During the deployment of the prosthesis with the use of the apical approach, the atrial anchoring points deploy first, making it possible to catch the annular tissue, then, secondly, over the course of the deployment, the ventricular anchoring points deploy in turn and make it possible to perfect the anchoring of the prosthesis, with maintenance of the anchoring points in the intra-annular position.

This "crab claw" allows very effective anchoring of the prosthesis inside the native valve annulus. Indeed, the proposed structure allows an implantation that bears on the peri-annular valve tissue first (the anchoring points), which is followed by additional bearing on the valve annulus. The claw catching system thus allows catching of the valve tissue and is completed by the intra-annular bearing of the metal structure, in the mitral and tricuspid position as required by the access used.

Said annular portion may in particular comprise six pairs of anchoring points.

Preferably, the bases of the anchoring points are connected to the portions of the meshes that form at the opposite corners of these meshes in the atrial-ventricular direction of the prosthesis, these anchoring points protruding from these portions of the meshes.

During the movement of said annular portion, said opposite corners of the meshes come closer to one another, which sees to the insertion of the anchoring points into the valve annulus, by closing the claw formed by each pair of anchoring points.

Advantageously, the frame comprises, on the side of the base of the ventricular extensions, V-shaped spacers connecting a lateral wire portion of one extension to the lateral wire portion of the adjacent extension.

These spacers see to the proper deployment of the ventricular extensions and allow a slightly reinforced rigidity of the frame at the base of the ventricular extensions, but without hindering the ability of this frame to be contracted radially.

BRIEF DESCRIPTION OF THE DRAWINGS

The invention will be well understood, and other features and advantages thereof will appear, in reference to the appended diagrammatic drawing, which shows, as a non-limiting example, one preferred embodiment of the prosthesis in question.

FIG. 1 is a side view thereof, slightly offset toward the atrial side of this prosthesis;

FIG. 2a is an enlarged view of a portion of the prosthesis as shown in FIG. 1, comprising anchoring claws;

FIG. 2b is a sectional view of the same portion, along an angle perpendicular to the view according to FIG. 2a;

FIG. 3 is a view of the prosthesis by its ventricular end, slightly off-centered, with the prosthetic valve comprised by this prosthesis in the open position;

FIG. 4 is a view thereof by its atrial end, with the prosthetic valve in the open position.

DETAILED DESCRIPTION

Figure 5:
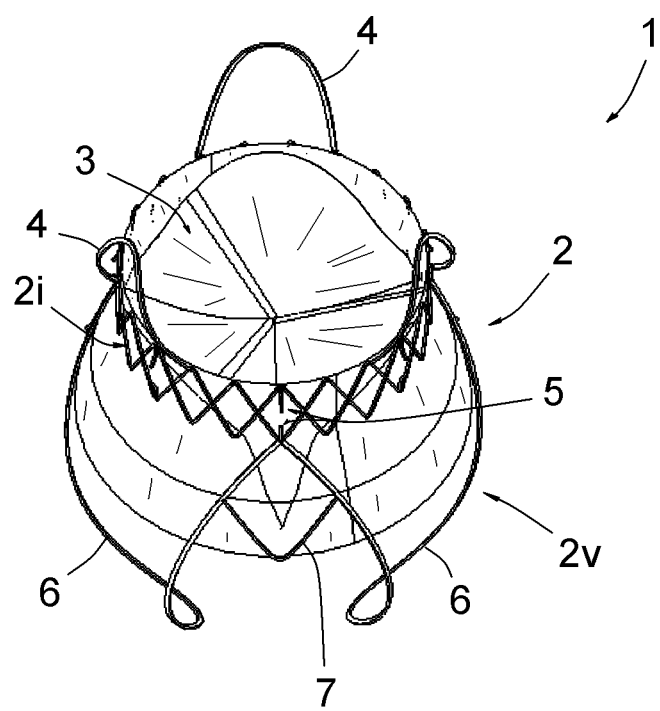
FIG. 5 is a view thereof similar to FIG. 4, with the prosthetic valve in the closed position.

The figures show a prosthetic mitral or tricuspid heart valve 1, comprising an expandable tubular frame 2 and a prosthetic valve 3 mounted on this frame.

The frame 2 has a structure made up of elastically deformable filaments, allowing it to assume the deployed form shown in the figures and a contracted form in which it can be contained in a catheter (not shown) for insertion into a heart. It may in particular be made, using a known technique, from a shape memory alloy, in particular nickel and titanium known as Nitinol.

The frame 2 comprises an atrial portion 2a, i.e., intended to be placed at the atrium of a heart, a ventricular portion 2v, i.e., intended to be placed at the ventricle of a heart, and an intermediate annular portion 2i, situated between these atrial 2a and ventricular 2v portions, intended to be placed at the native valve annulus.

The atrial portion 2a is made up of three metal-wire extensions 4, regularly distributed over its circumference and protruding from said annular portion 2i. Each extension 4 is made from a single wire, with an upside-down U or V shape, developing along a curved shape. In the expansion state of the prosthesis 1, shown in the figures, the base of each extension 4 is oriented radially toward the outside of the annular portion 2i, then the extension 4 curves toward the inside of the frame 2, such that the various extensions 4 are substantially part of an imaginary truncated sphere placed above said annular portion 2i.

The annular portion 2i is made up of diamond meshes connected to one another by their corners and comprises six pairs of anchoring claws 5 protruding from its outer face, regularly distributed over its perimeter. As is more particularly visible in FIGS. 2a and 2b, one claw 5 of a pair of claws has its base connected to the portion of the mesh that forms the corner of the mesh located on the atrial side of the prosthesis 1, and the other claw 5 of this same pair of claws has its base connected to the portion of the mesh that forms the corner of the mesh located on the ventricular side of the prosthesis, and the two claws 5 protrude from these portions of the mesh, toward one another; these claws 5 of each pair of claws are curved, with their concave side on the inside of this pair, such that the two claws 5 form a "crab claw", so as to form a sort of clamp. The claws 5 are curved and develop toward the outside of the prosthesis 1 from these bases toward their pointed free ends.

The ventricular portion 2v is made up of three metal-wire extensions 6, regularly distributed over its circumference and protruding from said annular portion 2i. Each extension 6 is made from a single wire, with an upside-down U or V shape, developing along a curved shape. In the expansion state of the prosthesis, the base of each extension 6 is oriented radially toward the outside of the annular portion 2i, then the extension 6 curves toward the inside of the frame 2, such that the various extensions 6 are substantially part of an imaginary truncated sphere placed below said annular portion 2i.

The frame 2 further comprises, on the side of the base of the extensions 6, V-shaped spacers 7 connecting a lateral wire portion of one extension 6 to the lateral wire portion of the adjacent extension 6.

The prosthetic valve 2 is of a known type, made from a synthetic or natural material (such as pig pericardium), and having three valves in the illustrated example.

In practice, the prosthesis 1 is contracted and placed in a catheter for insertion into a heart, which may be inserted into a heart through the apical approach. Because it comprises a mesh structure only at its annular portion 2i, made up of diamond meshes, and because of the aforementioned structure of the atrial 1a and ventricular 2v portions, this prosthesis 1 is able to assume a contracted shape with a small diameter, smaller than 18 mm in the contracted state. The catheter can therefore have an outer diameter of about 18 mm, the insertion of which is significantly less traumatic for the cardiac wall than a catheter according to the prior art.

When the prosthesis 1 is placed using the apical approach, its atrial portion 2a is first deployed and brought against the atrial part of the valve annulus; the substantially spherical shape of this atrial portion 2a is well suited to wide bearing against this atrial part of the annulus and against the adjacent wall of the atrium; said annular portion 2i is next deployed, which leads the different anchoring points comprised by this annular portion 5 to be inserted into the valve annulus. Good pre-positioning of the prosthesis 1 with respect to the implantation site is thus ensured.

The continued withdrawal of the catheter causes the gradual deployment of the ventricular portion 2v; this portion, in light of its ovoid shape, becomes closely applied against the ventricular part of the valve annulus and is well suited to the shape of the ventricle near this annulus; it does not conflict with the underlying anatomical structures. Furthermore, the independence of the extensions 6 allows the ventricular portion 2v not to present any risk of excessive bearing against the wall of the ventricle at the aortic valve, which could hinder the working of this aortic valve.

It should be noted that the prosthesis 1 could be implanted using a transseptal (mitral valve) or jugular or femoral (tricuspid valve) approach, in which case the ventricular portion 2v is deployed first and the atrial portion 2a is deployed second, with insertions of the claws 5 into the annulus being done in the same way as cited above.

The invention thus provides a prosthetic mitral or tricuspid heart valve having, relative to its counterpart prostheses of the prior art, the decisive advantages of being able to be inserted into a heart through an orifice having a diameter of about 18 mm, having very low migration risks, being easy to place, and having a shape suitable for the implantation site.

The invention has been described above in reference to one embodiment provided as an example. It is of course not limited to that embodiment but extends to all other embodiments covered by the appended claims.

What is claimed is:

1. A mitral or tricuspid heart valve prosthesis, comprising an expandable tubular frame and a prosthetic valve mounted on the frame, said frame comprising an atrial portion, a ventricular portion and an annular portion situated between the atrial and ventricular portions; the frame and the atrial portion, ventricular portion and annular portion have an inner side and an outer side and have a circumference; wherein:

said atrial portion is made up of three or four metal-wire atrial extensions, regularly distributed on the circumference of the atrial portion and projecting from said annular portion, each atrial extension being made up of a single upside-down U-shaped or V-shaped wire and having a base portion; each atrial extension develops with a curved shape such that, in the expansion state of the frame, the base portion of the atrial extension is oriented radially toward the outer side of said annular portion, and the atrial extension, above the base portion, curves toward the inner side of the frame, such that the atrial extensions are substantially part of an imaginary truncated sphere placed above said annular portion and are configured to provide a bearing against the atrial part of the annulus and against the adjacent wall of the atrium;

said annular portion has an outer face and is made up of diamond meshes connected to one another by their corners, which comprise anchoring points protruding from the outer face of the annular portion, wherein the anchoring points are configured to be inserted into the valve annulus; and said ventricular portion is made up of three or four metal-wire ventricular extensions, regularly distributed on the circumference of this ventricular portion and projecting from said annular portion, each ventricular extension being made up of a single U-shaped or V-shaped wire and having a base portion; each ventricular extension develops with a curved shape such that in the expansion state of the prosthesis, the base portion of the ventricular extension is oriented radially toward the outer side of said annular portion; each ventricular extension curves above said base portion toward the inner side of the frame, such that the various ventricular extensions are substantially part of an imaginary ovoid placed below said annular portion and are configured to be applied against the ventricular part of the valve annulus and are well suited to the shape of the ventricle near this annulus.

2. The prosthesis according to claim 1, wherein said anchoring points are in the form of curved claws having base portions and pointed free ends, each curved claw developing on the outer side of the said annular portion and away from the outer side of the said annular portion, from the base portion of the curved claw toward the pointed free end of the curved claw.

3. The prosthesis according to claim 1, wherein the anchoring points are present on the entire circumference of the annular portion.

4. The prosthesis according to claim 1, wherein the anchoring points are regularly distributed on the circumference of the annular portion.

5. The prosthesis according to claim 1, wherein the annular portion has an atrial side on the side of the atrial extensions and a ventricular side on the side of the ventricular extensions, and wherein the anchoring points have free ends and a concave side on the side of the annular portion; the anchoring points are arranged in pairs, such that one of the anchoring points of a pair is located on the atrial side and protrudes toward the ventricular side, and the other anchoring point of the same pair is located on the ventricular side and protrudes toward the atrial side, the free ends of these anchoring points being located opposite one another, and the anchoring points of the same pair being curved, with the concave side thereof such that the two anchoring points of the same pair of points assume the form of a "crab claw".

6. The prosthesis according to claim 5, wherein the annular portion comprises six pairs of anchoring points.

7. The prosthesis according to claim 5, wherein the anchoring points have base portions and each mesh of the annular portion have corner portions which are opposite one another in the direction from the atrial side to the ventricular side, and wherein the base portions of the anchoring points are connected to the corner portions of the meshes, these anchoring points protruding from these corner portions of the meshes.

8. The prosthesis according to claim 1, wherein the frame comprises, on the base portions of the ventricular extensions, V-shaped spacers connecting a lateral wire portion of one ventricular extension to the lateral wire portion of the adjacent ventricular extension.

* * * * *